United States Patent
Serna et al.

(10) Patent No.: US 9,622,891 B2
(45) Date of Patent: Apr. 18, 2017

(54) COATINGS FOR BRAIDED MEDICAL DEVICES AND METHODS OF FORMING SAME

(71) Applicant: Abbott Cardiovascular Systems Inc., Santa Clara, CA (US)

(72) Inventors: Benjamyn Serna, Gilroy, CA (US); Michael Huy Ngo, San Jose, CA (US); Syed F. A. Hossainy, Hayward, CA (US); O. Mikael Trollsas, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 20 days.

(21) Appl. No.: 14/687,843

(22) Filed: Apr. 15, 2015

(65) Prior Publication Data
US 2015/0297380 A1  Oct. 22, 2015

Related U.S. Application Data

(60) Provisional application No. 61/981,151, filed on Apr. 17, 2014.

(51) Int. Cl.
| | |
|---|---|
| *A61F 2/95* | (2013.01) |
| *B05D 1/38* | (2006.01) |
| *B05D 3/10* | (2006.01) |
| *B05D 3/12* | (2006.01) |
| *B05D 1/00* | (2006.01) |

(52) U.S. Cl.
CPC ............... *A61F 2/95* (2013.01); *B05D 1/38* (2013.01); *B05D 3/10* (2013.01); *B05D 3/12* (2013.01); *A61F 2210/0076* (2013.01); *A61F 2230/0063* (2013.01); *A61F 2240/001* (2013.01); *A61F 2250/0067* (2013.01); *A61L 2420/02* (2013.01); *B05D 1/002* (2013.01)

(58) Field of Classification Search
CPC ..... A61F 2/95; A61F 2210/0076; B05D 1/38; B01D 1/002
USPC ......................................... 427/2.24–2.31, 299
See application file for complete search history.

(56) References Cited

U.S. PATENT DOCUMENTS

| | | | |
|---|---|---|---|
| 4,655,771 | A | 4/1987 | Wallsten |
| 5,527,354 | A | 6/1996 | Fontaine et al. |
| 5,980,972 | A * | 11/1999 | Ding .................. A61L 33/0011 427/2.24 |

(Continued)

FOREIGN PATENT DOCUMENTS

| | | |
|---|---|---|
| CN | 101391115 | 3/2009 |
| EP | 2431066 A1 | 3/2012 |

OTHER PUBLICATIONS

Cai et al. "Synethesis and Characterization of Polycaprolactone (B)—Poly(lactide-co-glycolide) (A) ABA Block Copolymer," Polymers for Advanced Technologies, 2000, vol. 11, pp. 159-166.

(Continued)

*Primary Examiner* — Cachet Sellman
(74) *Attorney, Agent, or Firm* — Squire Patton Boggs (US) LLP

(57) ABSTRACT

Embodiments of the present invention encompass methods of forming coatings, particularly coatings for medical devices, and more particularly, for braided or woven medical devices. Embodiments of the present invention encompass the coatings and the coated devices. The coatings may include a polymer and optionally a therapeutic agent.

17 Claims, 3 Drawing Sheets

(56) References Cited

U.S. PATENT DOCUMENTS

| | | | |
|---|---|---|---|
| 6,007,574 A | 12/1999 | Pulnev et al. | |
| 6,110,483 A | 8/2000 | Whitbourne et al. | |
| 6,939,376 B2 | 9/2005 | Shulze et al. | |
| 7,018,401 B1 | 3/2006 | Hyodoh et al. | |
| 7,323,209 B1 | 1/2008 | Esbeck et al. | |
| 7,824,729 B2 | 11/2010 | Roorda et al. | |
| 8,221,821 B1* | 7/2012 | Weldon | A61F 2/86 427/2.1 |
| 8,231,929 B2 | 7/2012 | Sun | |
| 8,414,635 B2 | 4/2013 | Hyodoh et al. | |
| 8,419,788 B2 | 4/2013 | Sheldon et al. | |
| 8,642,062 B2 | 2/2014 | Trollsas et al. | |
| 8,661,630 B2 | 3/2014 | Lim et al. | |
| 8,689,728 B2* | 4/2014 | Adolfo | B05B 13/0442 118/500 |
| 2002/0035396 A1 | 3/2002 | Heath | |
| 2004/0024450 A1* | 2/2004 | Shulze | A61F 2/90 623/1.42 |
| 2004/0249444 A1* | 12/2004 | Reiss | B23H 9/008 623/1.15 |
| 2005/0049682 A1 | 3/2005 | Leanna et al. | |
| 2005/0106204 A1 | 5/2005 | Hossainy et al. | |
| 2006/0116752 A1 | 6/2006 | Norton et al. | |
| 2006/0121080 A1* | 6/2006 | Lye | A61F 2/07 623/1.39 |
| 2007/0259099 A1* | 11/2007 | Van Sciver | B05D 1/02 427/2.24 |
| 2009/0093870 A1* | 4/2009 | Menendez | B05D 1/02 623/1.11 |
| 2009/0148591 A1* | 6/2009 | Wang | A61L 31/10 427/2.25 |
| 2009/0228094 A1* | 9/2009 | Yan | A61F 2/91 623/1.12 |
| 2010/0209472 A1 | 8/2010 | Wang | |
| 2011/0129514 A1 | 6/2011 | Hossainy et al. | |
| 2011/0137243 A1 | 6/2011 | Hossainy et al. | |
| 2011/0190872 A1 | 8/2011 | Anukhin et al. | |
| 2012/0128863 A1 | 5/2012 | Nguyen et al. | |
| 2013/0230564 A1 | 9/2013 | Kleiner et al. | |

OTHER PUBLICATIONS

IDEV "Supera Peripheral Stent System," URL: http://www.idevmd.com/int-supera.html, copyright 2013, printed Oct. 4, 2013, 1 page.

Sawhney et al. "Rapidly degraded terpolymers of dl-lactide, glycolide and $_e$-caorolactone with increased hydrophilicity by copolymerization with polyethers," Journal of Biomedical Materials Research, 1990, vol. 24, pp. 1397-1411.

Zilver PTX Drug-Eluting Peripheral Stent "Drug elution has come to the periphery," URL: http://silverptx.cookmedical.com/us/index.html, copyright 2014, printed Jan. 8, 2016, 2 pages.

International Search Report and Written Opinion in PCT/US2015/026037, mailed Nov. 30, 2015, 26 pages.

Zilver PTX-Drug-Eluting Peripheral Stent "Instructions for Use" URL: http://silverptx.cookmedical.com/us/provenDrugEffect.html, copyright 2014, printed Jan. 8, 2016, 1 page.

* cited by examiner

COATINGS FOR BRAIDED MEDICAL DEVICES AND METHODS OF FORMING SAME

CROSS-REFERENCE TO RELATED APPLICATION

This application claims the benefit of, and hereby incorporates by reference as if fully set forth, expressly including any drawings, U.S. provisional patent application No. 61/981,151, filed on Apr. 17, 2014.

FIELD

This invention relates to the field of implantable medical devices (IMDs), more particularly to implantable medical devices having a coating from which drug(s) can be released at a target site in patient's body, and methods of forming the coatings on medical devices, particularly, braided medical devices.

BACKGROUND

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies) was coronary by-pass surgery. While effective, and having evolved to a relatively high degree of safety for such an invasive procedure, by-pass surgery still involves serious potential complications and, in the best of cases, an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, PTCA failed to satisfactorily ameliorate another problem, restenosis, the re-clogging of the treated artery.

The next improvement, advanced in the mid-1980s was use of a stent to scaffold the vessel walls open after PTCA. This for all intents and purposes put an end to elastic recoil, but did not entirely resolve the issue of restenosis. That is, prior to the introduction of stents, restenosis occurred in from 30-50% of patients undergoing PTCA. Stenting reduced this to about 15-30%, much improved, but still more than desirable.

In 2003, the drug-eluting stent (or DES) was introduced. The drugs initially employed with the DES were cytostatic compounds, compounds that curtailed the proliferation of cells that contributed to restenosis. As a result, restenosis was reduced to about 5-7%, a relatively acceptable figure. Today, the DES is the default industry standard for the treatment of atherosclerosis, and is rapidly gaining favor for treatment of stenoses of blood vessels other than coronary arteries such as peripheral angioplasty of the superficial femoral artery.

Endovascular intervention in the peripheral circulation has proven more problematic than in the coronary arteries as restenosis is still relatively common, especially in patients with long, complex occlusive lesions of the superficial femoral artery (SFA). Restenosis, mediated by the pathological process of neointimal hyperplasia, complicates roughly 40% of all peripheral vascular interventions after one year, leading a recent international consensus panel of cardiologists, vascular surgeons, and interventional radiologists to suggest that the current state-of-the-art of SFA stenting results in only 62% patency after one year.

Braided or woven stents may be useful in peripheral vessels. An example of a braided stent is the Wallsten stent, U.S. Pat. No. 4,655,771. To date, most of the DESs are not braided stents. Thus, there is a need for coatings and coating methods directed to braided medical devices, such as braided stents.

SUMMARY

The current invention is directed to coatings for medical devices, particularly braided medical devices, the coated devices, and methods of applying these coatings.

Various non-limiting embodiments of the present invention are presented in the following labeled paragraphs:

[A] Embodiments of the present invention include a method including preparing a coating composition comprising one or more solvents, one or more polymers, and optionally one or more therapeutic agents; subsequent to the preparation, applying the coating composition onto a medical device from an applicator to form a coating layer, the application comprising two or more passes; wherein the medical device has a lumen; wherein during each pass with respect to the applicator, the medical device axially translates; with respect to the applicator, the medical device rotates; or a combination thereof; wherein condition (1) applies, condition (2) applies, or both conditions (1) and (2) apply, and where the conditions are: (1) the diameter of the medical device varies during the application process, such that the largest diameter during any pass differs from the smallest diameter in any pass by at least 5%; (2) with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 5%.

[B] In some embodiments, such as described in paragraph [A], condition (1) applies.

[C] In some embodiments, such as described in paragraph [B], the medical device is held at a first diameter for at least one pass; and then, the medical device is held at a second diameter for at least one pass.

[D] In some embodiments, such as described in paragraph [B], the medical device, such as a stent, is held at a first diameter for at least five passes, and subsequently, the medical device is held at a second diameter for at least five passes.

[E] In some embodiments, such as described in paragraph [B], subsequent to holding the medical device at the first diameter for at least one pass; and holding the medical device at the second diameter for at least one pass, the medical device is held at the first diameter again for at least one pass; and following, the medical device is held at a second diameter again for at least one pass in the same order; and optionally, the sequence of holding the medical device at the first diameter for one or more passes followed by holding the medical device at the second diameter for at least one passes is repeated on one or more occasions.

[F] In some embodiments, such as described in paragraph [B], the variation is continuous.

[G] In some embodiments, such as described in paragraphs [B]-[F], the diameter of the medical device varies during the application process, the variation ranging such that the largest diameter during any pass differs from the smallest diameter in any pass by at least 10%.

[H] In some embodiments, such as described in paragraphs [B]-[F], wherein the diameter of the medical device varies during the application process, the variation ranging such that the largest diameter during any pass differs from the smallest diameter in any pass by at least 15%.

[I] In some embodiments, such as described in paragraphs [B]-[F], the diameter of the medical device varies during the application process, the variation ranging such that the largest diameter during any pass differs from the smallest diameter in any pass by at least 20%.

[J] In some embodiments, such as described in paragraphs [B]-[F], the diameter of the medical device varies during the application process, the variation ranging such that the largest diameter during any pass differs from the smallest diameter in any pass by at least 30%.

[K] In some embodiments, such as described in paragraphs [B]-[F], the diameter of the medical device varies during the application process, the variation ranging such that the largest diameter during any pass differs from the smallest diameter in any pass by at least 40%.

[L] In some embodiments, such as described in paragraphs [B]-[F], the diameter of the medical device varies during the application process, the variation ranging such that the largest diameter during any pass differs from the smallest diameter in any pass by at least 50%.

[M] In some embodiments, such as described in paragraphs [B]-[F], the diameter of the medical device varies during the application process, the variation ranging such that the largest diameter during any pass differs from the smallest diameter in any pass by at least 60%.

[N] In some embodiments, such as described in paragraphs [B]-[F], the diameter of the medical device varies during the application process, the variation ranging such that the largest diameter during any pass differs from the smallest diameter in any pass by at least 75%.

[O] In some embodiments, such as described in paragraphs [B]-[N], the diameter of the medical device varies during the application process, the variation ranging such that the largest diameter during any pass differs from the smallest diameter in any pass by not more than 90%.

[P] In some embodiments, such as described in paragraphs [B]-[N], the diameter of the medical device varies during the application process, the variation ranging such that the largest diameter during any pass differs from the smallest diameter in any pass by not more than 100%.

[Q] In some embodiments, such as described in paragraphs [B]-[N], the diameter of the medical device varies during the application process, the variation ranging such that the largest diameter during any pass differs from the smallest diameter in any pass by not more than 200%.

[R] In some embodiments, such as described in paragraphs [B]-[N], the diameter of the medical device varies during the application process, the variation ranging such that the largest diameter during any pass differs from the smallest diameter in any pass by not more than 500%.

[S] In some embodiments, such as that described in paragraph [B]-[R], the medical device is a braided stent; condition (1) applies; and the variation in the stent diameter results from stretching the stent, compressing the stent, or a combination of stretching and compressing the stent in the axial direction.

[T] In some embodiments, such as described in paragraphs [A]-[S], condition (2) applies.

[U] In some embodiments, such as described in paragraph [T], the medical device is twisted either counterclockwise or clockwise to an angular position and held for at least one pass, and the medical device twisted back partially, twisted back to the original conformation of no twist, or twisted back to the original conformation and subsequently twisted in the opposite direction, and held for at least one pass.

[V] In some embodiments, such as described in paragraph [T], the twisting is continuous.

[W] In some embodiments, such as described in paragraphs [T]-[V], with respect to one end of the medical device, such as a stent, the degree of twist of the other end varies during the application process, such that the difference between the largest degree of twist in one direction in any pass and the largest degree of twist in the reverse direction in any pass, or if no twist in the opposite direction, the smallest degree of twist in the same direction in any pass, is at least 10°.

[X] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 15°.

[Y] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 30°.

[Z] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 45°.

[AA] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 60°.

[AB] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 75°.

[AC] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 90°.

[AD] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 105°.

[AE] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 120°.

[AF] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 135°.

[AG] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 150°.

[AH] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 180°.

[AI] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 270%.

[AJ] In some embodiments, such as described in paragraphs [T]-[V], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 360°.

[AK] In some embodiments, such as described in paragraphs [T]-[AG], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is not more than 180°.

[AL] In some embodiments, such as described in paragraphs [T]-[AI], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is not more than 360°.

[AM] In some embodiments, such as described in paragraphs [T]-[AJ], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is not more than 540°.

[AN] In some embodiments of the present invention, such as described in paragraphs [T]-[AJ], with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is not more than 720°.

[AO] Embodiments of the present invention include a method comprising: preparing a coating composition comprising one or more solvents, one or more polymers, and optionally one or more therapeutic agents; wherein the combination of the one or more solvents has a viscosity of about equal to or greater than 45 cP, a surface tension of about equal to or greater than 45 mN/m, or both; subsequent to the preparation, applying the coating composition onto a medical device with a lumen from an applicator to form a coating layer.

[AP] In some embodiments, such as described in paragraph [AO], the combination of the one or more solvents has a viscosity of about equal to or greater than 95 cP or higher.

[AQ] In some embodiments, such as described in paragraph [AO], the combination of the one or more solvents has a viscosity of about equal to or greater than 145 cP or higher.

[AR] In some embodiments, such as described in paragraphs [AO]-[AQ], the combination of the one or more solvents has a viscosity of not more than 20,000 cP.

[AS] In some embodiments, such as described in paragraphs [AO]-[AR], the combination of the one or more solvents has a surface tension of about 50 mN/m or higher.

[AT] In some embodiments, such as described in paragraphs [AO]-[AR], the combination of the one or more solvents has a surface tension of about 55 mN/m or higher.

[AU] In some embodiments, such as described in paragraphs [AO]-[AR], the combination of the one or more solvents has a surface tension of about 65 mN/m or higher

[AV] In some embodiments, such as described in paragraphs [AO]-[AU], the combination of the one or more solvents has a surface tension of not more than 250 mN/m.

[AW] Embodiments of the present invention include a method comprising: applying one or more first solvents onto a medical device from an applicator; wherein the combination of the one or more first solvents has a viscosity of about equal to or greater than 45 cP, a surface tension of about equal to or greater than 45 mN/m, or both; and wherein the one or more first solvents are substantially free of other materials; preparing a coating composition comprising one or more second solvents, one or more polymers, and optionally one or more therapeutic agents; wherein each of the one or more second solvent may be the same as any one of the one or more first solvents, or may be different from each of the one or more first solvents; subsequent to the preparation, and the applying of the one or more first solvents, applying the coating composition onto a medical device from an applicator to form a coating layer.

[AX] In some embodiments, such as described in paragraph [AW], the combination of the one or more second solvents has a viscosity of about equal to or greater than 45 cP.

[AY] In some embodiments, such as described in paragraph [AW], the combination of the one or more first solvents, the one or more second solvents, or both, have a viscosity of about equal to or greater than 95 cP.

[AZ] In some embodiments, such as described in paragraph [AW], the one or more first solvents, the one or more second solvents, or both, have a viscosity of about equal to or greater than 145 cP.

[BA] In some embodiments, such as described in paragraphs [AW]-[AZ], the combination of the one or more first solvents, the one or more second solvents, or both, have a viscosity of not more than 20,000 cP.

[BB] In some embodiments, such as described in paragraphs [AW]-[BA], the combination of the one or more first solvents, the one or more second solvents, or both, have a surface tension of about 50 mN/m or higher.

[BC] In some embodiments, such as described in paragraphs [AW]-[BA], the combination of the one or more first solvents, the one or more second solvents, or both, have a surface tension of about 55 mN/m or higher.

[BD] In some embodiments, such as described in paragraphs [AW]-[BA], the combination of the one or more first solvents, the one or more second solvents, or both, have a surface tension of about 65 mN/m or higher.

[BE] In some embodiments, such as described in paragraphs [AW]-[BD], the combination of the one or more first solvents, the one or more second solvents, or both, have a surface tension of not more than 250 mN/m.

[BF] In some embodiments, such as described in paragraphs [A]-[BE], at least one polymer is selected from the group consisting of poly(ethylene glycol) (PEG), poly(ethylene-oxide), block copolymers of poly(ethylene-oxide) and poly(propylene oxide), poly(lactide-co-glycolide-co-caprolactone)-block-PEG-poly(lactide-co-glycolide-co-caprolactone) polymers, poly(trimethylene carbonate-co-glycolide)-block-PEG-block-poly(trimethylene carbonate-co-glycolide) polymers, polylactide-block-PEG-polylactide polymers, poly(trimethylene carbonate-co-glycolide)-block-PEG -poly(trimethylene carbonate-co-glycolide) polymers, and poly(lactide-co-glycolide)-block-PEG-blockpoly(lactide-co-glycolide) polymers.

[BG] In some embodiments, such as described in paragraphs [A]-[BF], the coating composition comprises at least one therapeutic agent.

[BH] In some embodiments, such as described in paragraphs [BG], the therapeutic agent is selected from the group consisting of dexamethasone, Biolimus A9, ridaforolimus, tacrolimus, temsirolimus, pimecrolimus, novolimus, myolimus, zotarolimus (ABT-578), 40-O-(2-hydroxyl)ethyl-rapamycin (everolimus), 40-O-(3-hydroxypropyl)rapamycin, 40-O-[2-(2-hydroxyl)ethoxy]ethyl-rapamycin, 40-O-tetrazolylrapamycin, 40-epi-(N1-tetrazolyl)-rapamycin, and combinations thereof.

[BI] In some embodiments, such as described in paragraphs [A]-[BH], the medical device is tubular or cylindrical in shape.

[BJ] In some embodiments, such as described in paragraphs [A]-[BI], the tubularly shaped medical device is a braided device.

[BK] In some embodiments, such as described in paragraphs [A]-[BJ], the medical device is a stent.

[BL] In some embodiments, such as described in paragraphs [A]-[BK], the coating composition, the solvents, or both are applied by spraying.

[BM] In some embodiments, such as described in paragraph [BL], the applicator is a spray nozzle.

DETAILED DESCRIPTION

DISCUSSION

Figure 1:
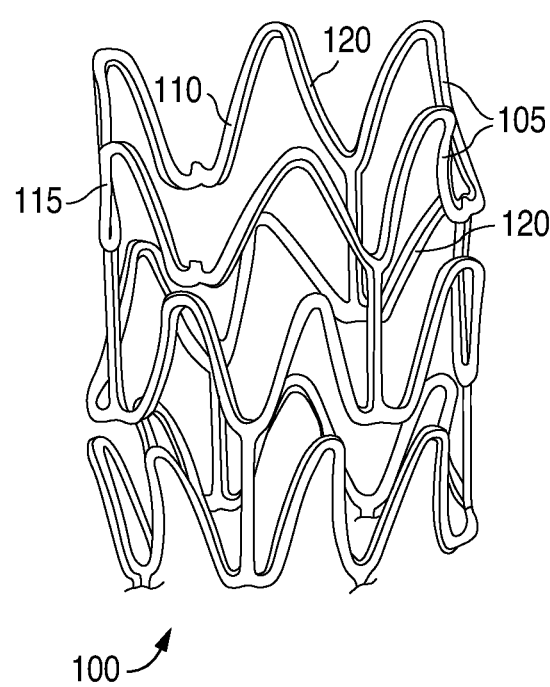
FIG. 1 depicts an exemplary stent.

Embodiments of the present invention encompass coatings disposed over the surface of a substrate, the substrate being a braided medical device, and methods of applying such coatings, as well as the coated devices. The coatings include a polymer, and optionally, a therapeutic agent.

Use of the singular herein, including in the claims, includes the plural and vice versa unless expressly stated to be otherwise. That is, "a" and "the" refer to one or more of whatever the word modifies. For example, "a drug" may refer to one drug, two drugs, etc. Likewise, "the stent" may refer to one, two or more stents and "the polymer" may mean one polymer or a plurality of polymers. By the same token, words such as, without limitation, "stents" and "polymers" would refer to one stent or polymer as well as to a plurality of stents or polymers unless it is expressly stated or obvious from the context that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. With the preceding discussion in mind, a numerical value herein that is modified by a word of approximation may vary from the stated value by ±15% in some embodiments, by ±10% in some embodiments, by ±5% in some embodiments, or in some embodiments, may be within the 95% confidence interval.

As used herein, any ranges presented are inclusive of the end-points. For example, "a temperature between 10° C. and 30° C." or "a temperature from 10° C. to 30° C." includes 10° C. and 30° C., as well as any temperature in between. In addition, throughout this disclosure, various aspects of this invention can be presented in a range format. It should be understood that the description in range format is merely for convenience and brevity and should not be construed as an inflexible limitation on the scope of the embodiments of the invention. Accordingly, the description of a range should be considered to have specifically disclosed all the possible subranges as well as individual numerical values within that range. As an example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" or "from" a first indicate number "to" a second indicate number are used herein interchangeably and are meant to include the first and second indicated numbers and all the fractional and integral numerals there between.

As used herein, a "therapeutic agent," refers to any substance that, when administered in a therapeutically effective amount to a patient suffering from a disease or condition, has a therapeutic beneficial effect on the health and well-being of the patient. A therapeutic beneficial effect on the health and well-being of a patient includes, but is not limited to: (1) curing the disease or condition; (2) slowing the progress of the disease or condition; (3) causing the disease or condition to retrogress; (4) alleviating one or more symptoms of the disease or condition; or a combination thereof.

As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; (3) preventing or delaying recurrence of the disease or condition after a course of treatment with a therapeutically effective amount of a substance, which may be the same as or different from the substance used in a prophylactically effective amount, has concluded; or a combination thereof.

As used herein, "therapeutic agent," also refers to pharmaceutically acceptable, pharmacologically active derivatives of those therapeutic agents specifically mentioned herein, including, but not limited to, salts, esters, amides, and the like.

As used herein, a "polymer" refers to a molecule comprised of, actually or conceptually, repeating "constitutional units." The constitutional units derive from the reaction of monomers. As a non-limiting example, ethylene ($CH_2=CH_2$) is a monomer that can be polymerized to form polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. The constitutional units themselves can be the product of the reactions of other compounds. A polymer may be derived from the polymerization of several different types of monomers or may be formed of several different types of constitutional units. Such polymers are referred to as "copolymers." "Terpolymers" are a subset of copolymers formed of three different types of constitutional units. Those skilled in the art, given a particular polymer, will readily recognize the constitutional units of that polymer and will equally readily recognize the structure of the monomer from which the constitutional units derive. As used herein, the term polymer refers to a molecule comprising more than 20 constitutional units.

Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. In other words, the polymers used in this invention may be regular alternating polymers, random alternating polymers, regular block polymers, random block polymers or purely random polymers unless expressly noted otherwise. Polymers may be cross-linked to form a network.

As used herein, a molecule which has a chain length of 20 or fewer constitutional units is referred to as an "oligomer."

As used herein, "solvent" is defined as a substance capable of dissolving one or more substances, capable of at least partially dissolving the substance(s), and/or dispersing one or more substances to form a uniformly dispersed solution at a selected temperature and pressure. A solvent can refer to one chemical compound, or a mixture of chemical compounds. A solvent can be a fluid.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, stent-expandable stents, stent-grafts, grafts, artificial heart valves, foramen ovale closure devices, cerebrospinal fluid shunts, orthopedic fixation devices, and intrauterine devices. While the preceding devices all have a primary function and, as a secondary function may be coated with a coating of an embodiment of this invention, an implantable medical device specifically designed and intended solely for the localized delivery of a therapeutic agent is also within the scope of this invention.

Other medical devices may be referred to as insertable medical devices that are any type of appliance that is totally or partly introduced, surgically or medically, into a patient's body or by medical intervention into a natural orifice, but the device does not remain in the patient's body after the procedure.

In general, the body of a medical device is the main or central portion of the device. For some medical devices the device body is the device in the fully functional form before a coating or other material different from that of which the body is formed has been applied or attached.

Implantable and insertable medical devices can be made of virtually any material including metals, polymers, or a combination of both. Devices or device bodies made from bioabsorbable polymers, biostable polymers, or a combination of both, could also be used with the embodiments of the present invention. The device can be, for example, a bioabsorbable stent. The material from which the device is manufactured is not a limitation with respect to the present invention.

One type of implantable medical device is a stent. Stents are implantable medical devices that are generally cylindrically shaped and function to hold open, and sometimes expand, a segment of a blood vessel or other vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease. A stent can be used in, without limitation, neuro, carotid, coronary, pulmonary, aorta, renal, biliary, iliac, femoral and popliteal, as well as other peripheral vasculatures, and in other bodily lumens such as the urethra or bile duct. A stent can be used in the treatment or prevention of disorders such as, without limitation, atherosclerosis, vulnerable plaque, thrombosis, restenosis, hemorrhage, vascular dissection or perforation, vascular aneurysm, chronic total occlusion, claudication, anastomotic proliferation, bile duct obstruction and ureter obstruction.

Another type of medical device is a vascular catheter. A vascular catheter may be an insertable device. A vascular catheter is a thin, flexible tube with a manipulating means at one end, referred to as the proximal end, which remains outside the patient's body, and an operative device at or near the other end, called the distal end, which is inserted into the patient's artery or vein. The catheter may be introduced into a patient's vasculature at a point remote from the target site, e.g., into the femoral artery of the leg where the target is in the vicinity of the heart. The catheter is steered, assisted by a guide wire than extends through a lumen, that is a passageway or cavity, in the flexible tube, to the target site whereupon the guide wire is withdrawn at which time the lumen may be used for the introduction of fluids, often containing therapeutic agents, to the target site. Some vascular catheters comprise multiple lumens allowing for introduction of fluids before the guidewire is removed. A catheter may also be used to deliver a stent or may be used to deliver a balloon used in angioplasty.

As used herein, a "balloon" refers to the well-known in the art device, usually associated with a vascular catheter, that comprises a relatively thin, flexible material, forming a tubular membrane, that when positioned at a particular location in a patient's vessel can be expanded or inflated to an outside diameter that is essentially the same as the inside or luminal diameter of the vessel in which it is placed. In addition to diameter, a balloon has other dimensions suitable for the vessel in which it is to be expanded. Balloons may be inflated, without limitation, using a liquid medium such as water or normal saline solution, that is, saline that is essentially isotonic with blood.

A "balloon catheter" refers to medical device which is system of a catheter with a balloon at the end of the catheter.

A balloon, a catheter, and a stent differ. Stents are typically delivered to a treatment site by being compressed or crimped onto a catheter or onto a catheter balloon, and then delivered through narrow vessels to a treatment site where the stent is deployed. Deployment involves expanding the stent to a larger diameter, typically to the diameter of the vessel, once it is at the treatment site. Stents can be self-expanding or balloon expandable. The expanded stent is capable of supporting a bodily lumen for an extended period of time. In contrast, a balloon has a wall thickness that is so thin that the tubular membrane cannot support a load at a given diameter unless inflated with a fluid, such as a liquid or gas. Furthermore, a balloon is a transitory device that is inserted in the patient's body for only a limited time for the purpose of performing a specific procedure or function. Unlike a stent, dilatation balloons are not permanently implanted within the body.

The structure of stents is typically a generally cylindrical or tubular form (but the precise shape may vary from the shape of a perfect cylinder), and may be perforated with passages that are slots, ovoid, circular or the like shape. In some embodiments, the perforations form at least 20%, preferably at least 30%, more preferably at least 35%, and more preferably at least 40%, but not more than 99% of the exterior surface area of the tube. A stent may be composed of scaffolding that includes a pattern or network of interconnecting structural elements or struts. The scaffolding can be formed from tubes, or sheets of material, which may be perforated or unperforated, rolled into a cylindrical shape and welded together to form a tube. A pattern may be formed in the tube by laser cutting, chemical etching, etc.

An example of a stent 100 is depicted in FIG. 1. As noted above, a stent may be a scaffolding having a pattern or network of interconnecting structural elements or struts 105, which are designed to contact the lumen walls of a vessel and to maintain vascular patency that is to support the bodily lumen. Struts 105 of stent 100 include luminal faces or surfaces 110, abluminal faces or surfaces 115, and side-wall faces or surfaces 120. The pattern of structural elements 105 can take on a variety of patterns, and the structural pattern of the device can be of virtually any design. Typical expanded dimensions of a coronary stent are 2 mm to 10 mm, preferably 1.5-6.0 mm, and length to diameter ratio is typically 2 to 25. For a stent, the device body is the scaffolding. The embodiments disclosed herein are not limited to stents, or to the stent pattern, illustrated in FIG. 1.

Figure 2:
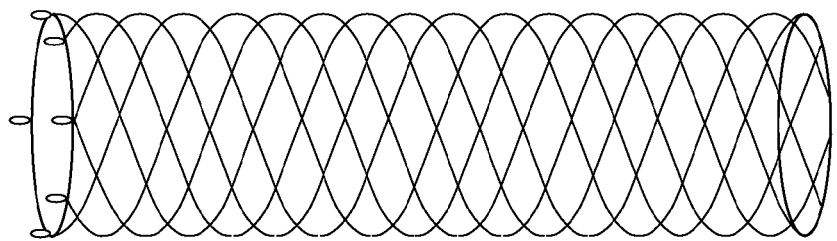
FIG. 2 depicts another type of exemplary stent, a braided stent.

Another type of stent is one formed of wires, such as the Wallsten stent, U.S. Pat. No. 4,655,771. A non-limiting example of a braided stent is shown in FIG. 2. The stents such as those described in U.S. Pat. Nos. 7,018,401 B1 and 8,414,635 B2, which are incorporated by reference herein (except if any definitions conflict, the definitions provided herein take precedence over definitions in U.S. Pat. Nos. 7,018,401 B1 and 8,414,635 B1), is a device that includes, but is not limited to, a plurality of shape memory wires woven together to form a body suitable for implantation into an anatomical structure. The body has first and second ends. The wires, preferably of a shape-memory material cross each other to form a plurality of angles, at least one of the angles being obtuse. Both ends of at least one wire are located proximate one end of the body. The value of the obtuse angle is increased when the body is axially compressed. The wires may be shape memory material such as and preferably, nitinol. The shape memory wires may also be made of FePt, FePd or FeNi—CoTi. The shape memory wires may be made of FeNiC, FeMnSi or FeMnSiCrNi. The shape memory wires may each have a diameter ranging in size from about 0.006 inches to about 0.012 inches. The plurality of shape memory wires may include at least 6 shape memory wires.

With respect to braided devices, the body may have a tubular shape with a substantially uniform diameter. The body may have a tapered shape with a diameter that decreases from one end of the body to the other end of the body. The body may have a generally hourglass shape. As used herein, "a generally hourglass" shape is a shape that resembles a body having two ends that are larger in terms of cross-sectional area than a mid-portion located there between. Such shapes include those resembling traditional hourglasses or dumbbells, for example. The body may be woven by hand. The body may be woven by a machine, such as a braiding machine.

Other stent forms include helical coils.

Braided or woven devices and stents are particularly suitable for treatment of a peripheral vessel. A device placed in a peripheral vessel is in a significantly different environment from a stent or device placed in a coronary vessel. The vessel size is larger. There is much more movement of the vessel, especially when located close to an appendage. As such, a device or stent intended for a peripheral vessel will need to be able to sustain more complex loading, including a combination of axial, bending, torsional and radial loading. See e.g. Bosiers, M. and Schwartz, L., Development of Bioresorbable Scaffolds for the Superficial Femoral Artery, SFA: CONTEMPORARY ENDOVASCULAR MANAGEMENT ('Interventions in the SFA" section). In contrast, stents or devices used to treat coronary vessels experience, for the most part, a primarily radial loading. These and related challenges facing peripherally implanted stents and scaffolds are also discussed in US2011/0190872.

A coating on a braided or woven stent intended to be placed in a peripheral vessel faces a number of challenges. As noted above, the implanted device is subject to complex loading, including a combination of axial, bending, torsional and radial loading. When the device bends or twists, the wires will move past each other. This type of bending and flexing will occur over the life of the device. Thus, the coating must be resistant to abrasion, and fatigue.

As used herein, a material that is described as "disposed over" an indicated substrate refers to, e.g., a coating layer of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer" and "coating layer" will be used interchangeably herein. A "layer" or "coating layer" of a given material is a region of that material whose thickness is small compared to both its length and width (e.g., the length and width dimensions may both he at least 5, 10, 20, 50, 100 or more times the thickness dimension in some embodiments). As used herein a layer need not be planar, for example, taking on the contours of an underlying substrate. Coating layers can be discontinuous. As used herein, the term "coating" refers to one or more layers deposited on a substrate. A coating layer may cover all of the substrate or a portion of the substrate, for example a portion of a medical device surface. A coating layer does not provide a significant fraction (<5%) of the mechanical support for the device. In some embodiments, the layers differ from one another in the type of materials in the layer, the proportions of materials in the layer, or both. In some embodiments, a layer may have a concentration gradient of the components. One of skill in the art will be able to differentiate different coating layers or regions from each other based on the disclosure herein.

As used herein, "above" a surface or layer is defined as further from the substrate measured along an axis normal to a surface, or over a surface or layer, but not necessarily in contact with the surface or layer.

As used herein, "below" a surface or layer is defined as closer to the substrate measured along an axis normal to a surface, or under a surface or layer, but not necessarily in contact with the surface or layer.

Coating layers may be applied by any number of methods including spraying, dipping, electrostatic coating, chemical vapor deposition, use of a controlled-volume ejector, extrusion, molding, lamination, direct fluid application, or any combination thereof. A coating layer can be formed from a single-pass application or multiple-pass application, where a "pass" can be any single process step or single application step, or combination of steps, used to apply a coating material. Examples of a pass include a pass of a spray coating device, a pass of an electrostatic coating device, a pass of a controlled-volume ejector, a dipping, an extrusion, a mold, a single dip in a layered manufacturing process, etc. In general, a pass includes any single process step known to one of skill in the art that can be used to apply materials to form a layer. Some coating layers comprise multiple passes. Materials may migrate between coating layers during application and/or after the coating is formed.

Embodiments of the present invention encompass methods of forming coatings, and the coated devices; including devices having a coating resulting from the application of the coating materials described herein, where the coating may be one layer or multiple layers. As used herein, a "primer layer" refers to a coating layer including a material, such as a polymer, that exhibits good adhesion characteristics with regard to the material of which the substrate is manufactured and whatever material is to be coated on the substrate. Thus, a primer layer serves as an adhesive intermediary layer between a substrate and materials to be carried by the substrate and is, therefore, applied directly to the substrate. In some embodiments, the primer layer as applied is free of any therapeutic agents, is formed from a composition free of any therapeutic agents, or both. As used herein, "drug reservoir layer" refers to a layer that includes one or more therapeutic agents. The layer may comprise one or more therapeutic agents applied neat (without any other materials), applied with an excipient such as a binder, or in combination with another material, such as, without limitation, a polymer in which the therapeutic agent would be a component of a polymer matrix.

Embodiments of the invention encompass coatings, devices including coatings, and methods of forming coatings of one or more layers with no drug, coatings with one or more drug reservoir layers, any number (including zero) of coating layers below the drug reservoir layer(s), any number of layers (including zero) above the drug reservoir layer(s), any number of coating layers (including zero) between the multiple drug reservoir layers, if more than one drug reservoir layer, and all combinations of the above. Embodiments of the present invention encompass devices having a coating formed by the application of one or more coating layers as described herein.

In some embodiments, optionally in combination with any of the other embodiments described herein, the coating may be disposed over all, or substantially all, of the surface of the substrate, such as the outer surface of the device body of an implantable or an insertable medical device. In some embodiments of the present invention, optionally in combination with any of the other embodiments described herein, the coating may be disposed over only part of or portions of the substrate.

Embodiments of the present invention, optionally in combination with any of the other embodiments described herein, encompass a total coating thickness from 0.2 microns to 50 microns, preferably 0.5 microns to 25 microns, and more preferably 1 micron to 15 microns. For an individual coating layer, the thickness may range from 0.2 microns to 50 microns, preferably 0.5 microns to 25 microns, and more preferably 1 micron to 15 microns. A micron is $10^{-6}$ meter, one millionth of a meter. Typically, the coating thickness is essentially uniform, but in some embodiments, the coating thickness is not uniform.

For coatings on a braided device, such as a braided stent, a thinner coating may be more resistant to abrasion and fatigue. In some embodiments, optionally in combination with any of the other embodiments described herein, the total coating is between 0.2 and 6 microns in thickness. In some embodiments, the coating excludes a primer layer. In some embodiments, optionally in combination with any of the other embodiments described herein, the weight ratio of therapeutic agent to polymer in a drug reservoir layer of the coating is 1:7 to 4:1 or about 1:7 to about 4:1, and preferably 1:3 to 3:1 or about 1:3 to about 3:1. As a braided or woven medical device, such as a stent, has more surface area per unit length than a medical device, such as a stent, formed by cutting or etching a pattern in a tube (a non-braided device), for a given length of the device, the therapeutic agent loading is higher if coated at the same thickness and therapeutic agent to polymer ratio that is used for a non-braided device formed by cutting or etching a pattern in a tube. Thus, in some embodiments, optionally in combination with any of the other embodiments described herein, a lower therapeutic agent to polymer weight ratio may be used to obtain the same quantity of therapeutic agent per unit length, or a thinner coating if the therapeutic agent to polymer ratio used is the same, or a combination thereof.

Figure 3:
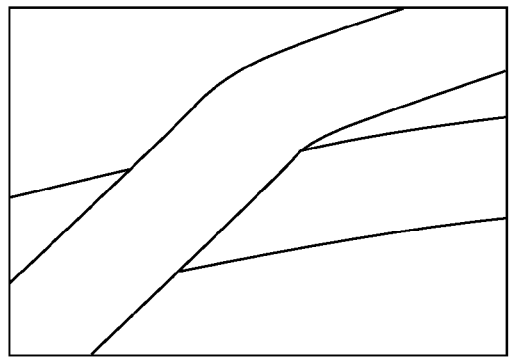
FIG. 3 depicts a junction point in a braided medical device.

As shown in FIG. 2, the wires forming a braided medical device, such as a stent, cross over each other. A close-up of the cross-over of the wires is shown in FIG. 3. These cross-over points are referred to as "junctions" or "junction points." For methods of application such as spraying and electrostatic deposition, the wires may not be coated on all sides. The percent of the outer surface of the device, such as a stent, involved in the junctions is estimated to be less than 10%. In general, with respect to implantable medical devices, the "outer surface" is meant any surface however spatially oriented that is in contact with bodily tissue or fluids. For a braided medical device, such as a stent, the "outer surface" is the total surface area of all of the wires used to form the medical device body that may be exposed to fluid if the medical device is flexed or moved.

Embodiments of the present invention provide methods for coating medical devices. These methods are particularly advantageous for coating medical devices such as braided stents, and other braided devices, such as, without limitation, vena cava filters and occluders.

Figure 4A:
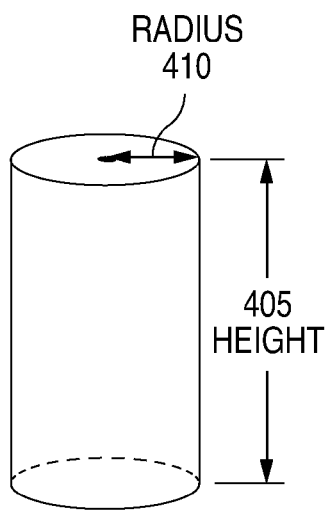
FIGS. 4A and 4B depict cylinders.
Figure 4B:
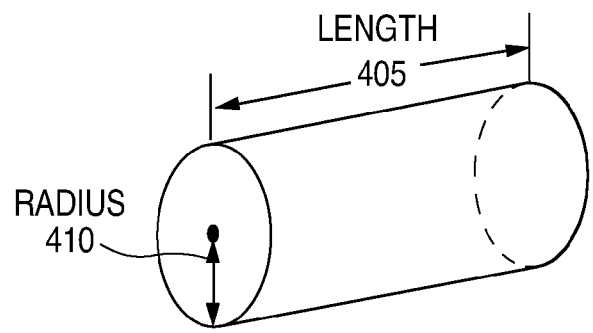

In the following discussion of the embodiments of the present invention reference may be made to a stent, or a cylindrically shaped medical device, but embodiments of the invention are not so limited. The various embodiments of the invention encompass stents as well as other medical devices. In general, embodiments of the present invention involving coating application, such as by spray coating, are applicable to medical devices with a lumen. A "lumen" as defined by Webster's Medical Dictionary is the channel within a tube such as a blood vessel, or the interior of a hollow organ such as the intestine. The term lumen is usually an anatomical term. As used herein, the term "lumen" may be broader because it may not only refer to the anatomy of an animal, but may also refer to the channel inside a tube or a tubular shaped object. Particularly suitable devices are those that are shaped like a hollow cylinder, or tube. A true cylinder has two identical ends which are circles or ellipses joined by one curved surface, and the cross-section is the same from one end to the other ("math is fun"). A true cylinder is characterized by a height (or length) 405 and a radius 410 as shown in FIGS. 4A and 4B. Particularly suitable devices are not limited to those corresponding to a hollow true cylinder, but the cross-section may vary in area from one end to the other, and the two "ends" which are typically open, may be of different shapes or may have different surface areas. Particularly suitable devices are those that have a height (or length) at least 50% of the largest radius, and preferably not more than fifteen (15) times the largest radius.

A number of coating application methods involve the use of a solvent. For example, coating materials, such as but not limited to, a polymer, a therapeutic agent, or both, may be dissolved, partially dissolved, dispersed, or a combination of dissolved and dispersed in a solvent (a fluid) to form a coating solution. The coating solution is disposed over the surface of the device and the solvent is removed or evaporates. Spraying, brushing, dipping, and direct fluid application are non-limiting examples of coating application methods using a solvent. Such coating procedures are well-known in the art.

In some embodiments, before the coating solution is disposed over the surface of the device, the device surface is pre-wet with a fluid with a low surface tension, a lower viscosity, or both. As used herein, a "low surface tension" is a fluid having a surface tension when measured at 20° C. of about equal to 30 mN/m or less than 30 mN/m, but not less than 0.1 mN/m. As used herein, a "low viscosity fluid" is a fluid having a dynamic viscosity at 20° C. of about equal to 1.5 centiPoise (cP), or less than 1.5 centiPoise, and at least 0.001 centiPoise. In some embodiments, the "low viscosity fluid" has a dynamic viscosity at 20° C. of 0.5 cP or less than 0.5 cP, but not less than 0.02 cP. In some embodiments, the viscosity, the surface tension, or both are determined at 20° C. and one atmosphere pressure. Non-limiting examples of such fluids include hexane, tetrahydrofuran (THF), 1-butanol, n-butyl acetate, acetone, ethanol, and benzene. Combinations of fluids may be used provided that the above conditions are met.

In some embodiments, application of the coating solution to the device surface is accomplished by spraying a solution onto a surface of the device, such as a stent. Typically, spraying involves atomizing the solution with a compressed gas (non-limiting examples of compressed gases include, air, nitrogen, and argon, but other gases, especially inert gases, may be used; or a supercritical fluid may be used). Important aspects of the spray coating process include the pressure of the atomizing gas and the spray nozzle to part distance. As noted above, multiple passes under the sprayer and dryer may be required to obtain a coating layer.

After the solution has been disposed over the device surface, the solvent is removed, or substantially removed, by evaporation. When the solvent is removed, what is left is the solid layer comprising the substances dissolved in the coating solution. The process of solvent removal can be accelerated by using an elevated temperature, lower pressure, using a flow of a gas or supercritical fluid over or past the device surface, or a logical combination thereof. As used herein, the phrase "solvent is removed" includes allowing the solvent to evaporate as well as using some means to increase the rate of evaporation. The layer remaining after solvent has been substantially removed may include a small amount (not more than 0.5 weight %, preferably, not more than 0.1 weight %, more preferably, not more than 0.05 weight %, and even more preferably, not more than 100 ppm by weight) of residual solvent as removal of absolutely all of the solvent may be very difficult.

Figure 5:
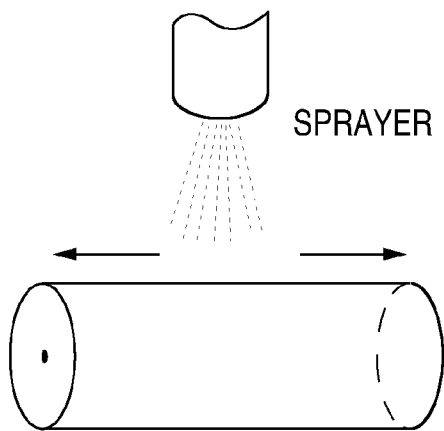
FIG. 5 depicts longitudinal translation of a cylinder.

During the application of the coating solution and the removal of solvent, the device may be rotated and translated. In some embodiments of the invention, for the application of a coating, the device may be mounted on a support allowing for translation along the longitudinal axis and rotation around the longitudinal axis. In order to ensure complete coating of the junctions, the rate of longitudinal translation may be decreased. As used herein, the longitudinal translation means movement from side to side or in other words, from left to right. Longitudinal translation is measured relative to the applicator so that the applicator may move from side to side along the length of the device, the device may move from side to side, or both. An example is illustrated in FIG. 5 with arrows showing the motion of the medical device, in this case a stent, assuming the applicator, such as a sprayer, is fixed in position. As an example, the rate of longitudinal translation may be from about 1 mm/s to about 5 mm/s, from 1 mm/s to 5 mm/s, preferably, from about 1.5 mm/s to about 4.5 mm/s, from 1.5 mm/s to 4.5 mm/s, more preferably from about 2 mm/s to about 4 mm/s, from 2 mm/s to 4 mm/s, and most preferably from about 2.5 mm/s to about 3.5 mm/s, from 2.5 mm/s to 3.5 mm/s.

As noted above, in embodiments of the invention, the device may be mounted on a support allowing for translation along the longitudinal axis and rotation around the longitudinal axis. In some embodiments, the device is rotated and translated during the coating application (such as, but not limited to spraying). Rotation around the longitudinal axis is illustrated by the arrow in FIG. 6 using a cylinder to represent the device.

In some embodiments, the diameter of the medical device may be altered during the coating process. For a woven or braided device, the device may be lengthened by applying a force at each end with a decrease in the diameter. This lengthening of the device moves the wires so the junctions occur at different points on the wires. The change in the diameter may occur in discrete steps. As an example, a number of passes of coating material, such as, without limitation, a number of passes of an applicator such as a sprayer during application onto the device, may be applied with the device at a diameter of 7 mm, then subsequently the device may be lengthened resulting in a device with a diameter of 3 mm, and another number of passes applied where the number of passes at each diameter may be the same, or different. The device may have coating material applied at multiple diameters, for example 7 mm, 5 mm, and 3 mm, where the number of application passes at each diameter may all be the same, or for at least one diameter, the number of passes may differ, or for all diameters, the number of passes may differ. The device may be at a first diameter for a set number of passes, then at a second larger or smaller diameter for a second number of passes, that may be the same or different than the set number of passes at the first diameter, and subsequently, the device may be at the first diameter again for a number of passes which may be the same number of passes as previously at the first diameter, the same number of passes as at the second diameter, or a different number of passes. The diameter may alternate between a large and a small diameter with a number of passes at the large diameter followed by a number of passes at the small diameter, and this may repeat one or more times with the same diameters and number of passes or with different diameters, different number of passes for each repetition, or a combination thereof. In general, there can be any number of diameters between the largest and the smallest diameters, there can be any number of application passes at each diameter, and the diameters may alternate or occur in any order.

The variation in diameter may occur continuously, that is the device is being lengthened or shortened at the same time the coating material is applied, that is during one or more passes, or a part or fraction of a pass. The variation may occur discretely as discussed above where the device is at a given diameter/length for one or more passes and then is changed to a different diameter/length before beginning the next pass or series of passes. The variation may be semi-continuous. As an example, for a number of passes the diameter/length may be set and remain essentially the same, then over one or more passes, the diameter/length may change to a second diameter, and then a number of passes may be executed at the second diameter. Embodiments of the present invention encompass any combinations of and variations of continuous, semi-continuous, or discrete application of the coating material at different diameters including variation in the rate of change of the diameter.

For some embodiments of the present invention, the device diameter differs by at least 5% from the smallest diameter during any pass of the coating application to the largest diameter during any pass. It is understood that the smallest diameter and the largest diameter may occur in the same pass. With respect to devices of non-constant diameter, the device diameter change will refer to the same reference diameter, such as, without limitation, the smallest diameter on the device, the largest diameter on the device, or the mid-point diameter on the device. For example, the smallest "smallest" diameter is compared to the largest "smallest" diameter. One of skill in the art will be able to determine an appropriate reference diameter based on the disclosure herein. In some embodiments, the diameter of the medical device varies during the application process, the variation ranging such that the largest diameter during any pass differs from the smallest diameter in any pass by at least 10%, by at least 15%, by at least 20%, by at least 30%, by at least 40%, by at least 50%, by at least 60, or by at least 75%. In some embodiments, the variation ranges such that the largest diameter during any pass differs from the smallest diameter in any pass by not more than 90%, not more than 100%, not more than 200%, or not more than 500%.

Figure 6:
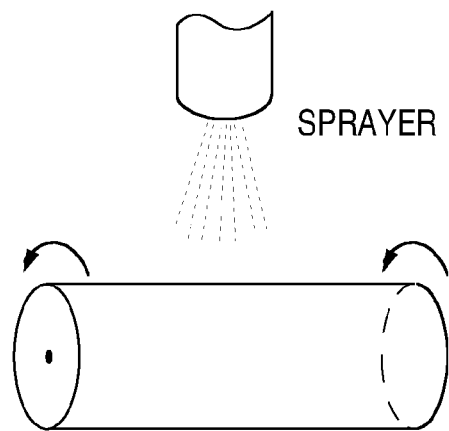
FIG. 6 depicts rotation of a cylinder.
Figure 7A:
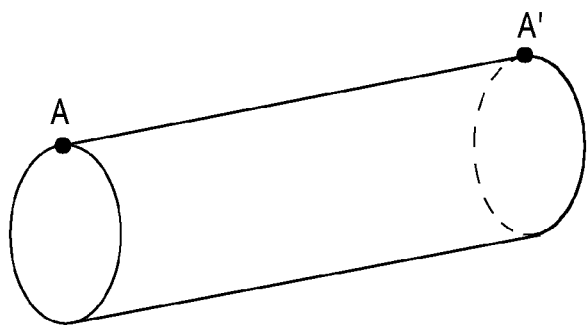
FIGS. 7A and 7B depict twisting of a cylinder.
Figure 7B:
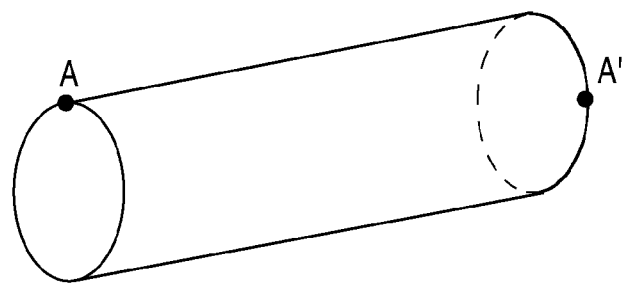
Figure 7C:
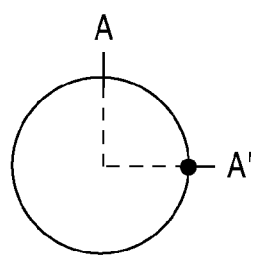
FIG. 7C depicts the end of the twisted cylinder.

In some embodiments, the medical device may be twisted or torqued during the coating process. As discussed above, the device may be rotated around its longitudinal axis as shown in FIG. 6. Twisting may be superimposed on top of rotation or may be executed independently of rotation. Twisting occurs when the ends of the device are rotated around the longitudinal axis at different rates and/or directions, or alternatively, one end is rotated while the other end is fixed. An example is illustrated in FIGS. 7A-7C, with reference to a cylinder using points labeled A and A' on each end of an exemplary medical device, which is a stent in this example. As shown in FIG. 7B and FIG. 7C, point A' is twisted or torqued by an angle of approximately 90° with respect to point A at the other end. This angle, shown here as about 90° will be referred to as the degree of twist. The change in twist of the stent moves the wires so the junctions occur at different points on the wires.

As an example, a number of passes may be applied with the device with one end being twisted (relative to the other end) by 90°, then subsequently the device may be twisted back to the original position (no twist), and another number of passes applied where the number of passes at each degree of twist may be the same or different. The device may have coating material applied at multiple degrees of twist, for example 0°, 90°, and 180°, where the number of application passes at each degree of twist may all be the same, or for at least one degree of twist, the number of passes may differ, or for all degrees of twist, the number of passes may differ. The device may be at a first degree of twist for a set number of passes, then at a second degree of twist that is either larger or smaller than the first, or the same or different magnitude in the opposite direction, for a second number of passes, that may be the same or different than the set number of passes at the first degree of twist, and subsequently, the device may be at the first degree of twist for a number of passes which may be the same number of passes as previously at the first degree of twist, the same number of passes as at the second degree of twist, or a different number of passes. The degree of twist may alternate between a first and a second degree of twist where the second degree of twist may be a different magnitude in the same direction, no twist, or a twist in the opposite direction, with a number of passes at the first degree of twist followed by a number of passes at the second degree of twist, and this may repeat one or more times with the same first and second degrees of twist and number of passes or with at least the first or second degree of twist being different, different number of passes for the first and second degrees of twist for each repetition, or a combination thereof. In general, embodiments of the invention encompass any number of degrees of twist between the maximum difference between the degrees of twist, there can be any number of application passes at each degree of twist, and the degrees of twist may alternate or occur in any order.

In some embodiments, the variation in the degree of twist occurs continuously, that is the device is being twisted at the same time the coating material is applied (during one or more passes, or a fraction of a pass). In some embodiments of the invention the variation occurs discretely as discussed above where the device is at a degree of twist for one or more passes (or a fraction of a pass) and then is changed to a different degree of twist before beginning the next pass or series of passes. In some embodiments, the variation in the degree of twist may be semi-continuous. As an example, for a number of passes the degree of twist may be set and remain essentially the same, then over one or more passes (or part of a pass), the device may be twisted to another degree of twist, and then a number of passes (or part of a pass) may be executed at the second degree of twist. It is understood that the degree of twist includes no twist, and the difference in the degree of twist for 90° clockwise and 90° counter-clockwise is 180°.

In some other embodiments, with respect to one end of the medical device, such as a stent, the degree of twist of the other end varies such that the maximum difference between the largest degree of twist in one direction in any pass and the largest degree of twist in the opposite direction in any pass or alternatively, the smallest degree of twist in the same direction if not twisted in the opposite direction, is at least 10°. The largest and smallest degree of twist of the device may occur in the same pass. In some embodiments, with respect to one end of the medical device, the degree of twist of the other end varies such that the maximum difference between the largest degree of twist in one direction (clockwise or counter-clockwise) in any pass and the largest degree of twist in the opposite direction in any pass, or alternatively, the smallest degree of twist in the same direction if not twisted in the opposite direction during any pass, is at least 15°, is at least 30°, is at least 45°, is at least 60°, is at least 75°, is at least 90°, is at least 105°, is at least 120°, is at least 135°, is at least 150°, is at least 180°, is at least 270°, or is at least 360°. It is understood that the smallest degree of twist includes zero (no twist), and that the maximum difference may occur within the same pass. In some embodiments, with respect to one end of the medical device, the degree of twist of the other end varies such that the maximum difference between the largest degree of twist in one direction (clockwise or counter-clockwise) in any pass and the largest degree of twist in the opposite direction in any pass, or alternatively, the smallest degree of twist in the same direction if not twisted in the opposite direction during any pass, is not more than 180°, not more than 360°, not more than 540°, or not more than 720°.

In some embodiments of the invention, the device is both twisted and the diameter changes during the coating application, that is the device is not at the same diameter and/or same degree of twist for all coating passes, including throughout each of the coating passes. Any combination of variation in the diameter/length and degree of twist may be used. As examples, both the diameter and the degree of twist may be changed continuously, both changed discretely, both changed semi-discretely, or any combination where one is changed in one manner, that is discretely, continuously, or semi-continuously, and the other is changed in a different manner.

In some embodiments, the coating is not a conformal coating (a coating covering all, or at least 98%, of the outer surface of the device) and the area around the junctions is left un-coated. In some embodiments, prior to disposing a coating solution over the surface of a braided medical device, the surface is pre-wetted such as by immersion or spraying, with a high viscosity and/or high surface tension solvent. It is believed that the high viscosity, high surface tension solvent, or solvent of both high viscosity and surface tension will not wet or will minimally wet the junctions. In some embodiments, a "high viscosity solvent" is one with a dynamic viscosity (at 20° C.) of about 45 cP or higher, about 95 cP or higher, or about 145 cP, or higher. As used herein, a "high surface tension solvent," is one with a surface tension of about 45 mN/m or higher. In some embodiments, a high surface tension solvent has a surface tension of about 50 mN/m or higher, about 55 mN/m or higher, or about 65 mN/m or higher. In some embodiments, the solvent of the coating solution has a viscosity (at 20° C.) of about 45 cP or higher, about 95 cP higher, or about 145 cP or higher, but not more than 20,000 cP, a surface tension of about 45 mN/m or higher, about 55 mN/m or higher, or about 65, mN or higher, but not more than 250 mN/m, or any combination of the previously listed viscosity and surface tensions. In some embodiments, the solvent viscosity, surface tension, or both are measured at 20° C. and a one atmosphere pressure. In some embodiments, the solvent for the coating solution is a high viscosity solvent, a high surface tension solvent, or both.

In some embodiments, application of the coating solution to the medical device, such as a stent, is accomplished by mounting the medical device on a support such as a mandrel. In some embodiments, the medical device may fit snugly onto a mandrel and vibration of the medical device limited or eliminated to keep the junctions from moving. Thus, it is expected the area between the junctions would remain uncoated. As compared to an unbraided medical device, such as a stent, the area of contact between the braided medical device and the mandrel is less due to the lower contact area of the wires. Thus, it is expected that sticking would not be an issue, or there would be less sticking, at least 30% less, for a braided medical device than would occur with an unbraided medical device.

In other embodiments, the junctions are masked, that is covered, prior to the application of a coating material such as by spraying a coating solution. A mask is a physical barrier covering the junctions. It is believed that by leaving the junctions uncoated the issues with abrasion are avoided, or minimized. The junctions occupy less than 10% of the surface area of the braided device, and thus there would still be sufficient surface area for drug delivery. In some embodiments, only the abluminal surface is coated.

Polymers

Representative examples of polymers, oligomers, and materials that may be used, either individually or in combination, in the various embodiments of coatings described herein, and optionally, may be used in forming a device body, include, without limitation, polyesters, polyhydroxyalkanoates, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyhydroxybutyrate, polyhydroxybutyrate-co-hydroxyvalerates, polyhydroxybutyrate-co-hydroxyhexanoate, polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(D-lactide-co-caprolactone), poly(D-lactide), poly(glycolide-co-caprolactone), poly(trimethylene carbonate), polyester amides, poly(glycolic acid-co-trimethylene carbonate), poly(amino acid)s, polyphosphazenes, polyolefins, polyisobutylene and ethylene-alphaolefin copolymers, acrylic polymers and copolymers, polyacrylates, polymethacrylates, poly(butyl methacrylate), 2-hydroxyethyl methacrylate (HEMA), hydroxypropyl methacrylate (HPMA), hydroxypropyl methacrylamide; polymers and copolymers of PEG acrylate (PEGA), PEG methacrylate, 2-methacryloyloxyethylphosphoryl-choline (MPC), methacrylic acid (MA), acrylic acid (AA), alkoxymethacrylate, alkoxyacrylate, and 3-trimethylsilylpropyl methacrylate (TMSPMA); polyhydroxyacrylates, vinyl halide polymers and copolymers (such as polyvinyl chloride), polyvinyl ethers (such as polyvinyl methyl ether), polyvinylidene halides (such as polyvinylidene chloride and polyvinylidene fluoride which is otherwise known as KYNAR™, available from Atofina Chemicals, Philadelphia, Pa.), polyvinyl ketones, polyvinyl aromatics (such as polystyrene), polyvinyl esters (such as polyvinyl acetate), polyvinylbutyral (such as BUTVAR™ B-79 sold by Monsanto), acrylonitrile-styrene copolymers, ABS resins, polyamides (such as Nylon 66 and polycaprolactam), polymers and copolymers of N-vinyl butyrolactam, polymers and copolymers of N-vinyl caprolactam, polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, ethylene vinyl alcohol copolymer (commonly known by the generic name EVOH or by the trade name EVAL™), poly(styrene-isoprene-styrene)-block-PEG (SIS-PEG), polystyrene-block-PEG, polyisobutylene-block-PEG, poly(methyl methacrylate)-block-PEG (PMMA-PEG), polydimethylsiloxane-co-PEG (PDMS-PEG), poly(vinylidene fluoride-co-hexafluoropropene) (for example, without limitation, SOLEF 21508™, available from Solvay Solexis PVDF, Thorofare, N.J.), poly(tetramethylene glycol), hydroxy functional poly(vinyl pyrrolidone), ethylene-vinyl acetate copolymers, styrene-isobutylene-styrene triblock copolymers, copolymers of vinyl pyrrolidone and vinyl acetate, melamine resins such as hexamethoxymethyl-melamine, epoxies such as EPON™ (Shell) 1001, polymers of sodium styrene sulfonate monomer, polymers of 2-acrylamido-2-methylpropane sulfonic acid, polymers of sodium vinyl sulfonate, poly(vinyl pyridine), and copolymers of vinyl compounds and hydroxyacrylates or acrylic acid, silicone, poly(dimethyl siloxane), and blends and copolymers thereof.

As used herein, the terms poly(D-lactide), poly(D,L-lactide), poly(L-lactide), poly(D-lactide-co-glycolide), poly(D,L-lactide-co-glycolide), and poly(L-lactide-co-glycolide) are used interchangeably with the terms poly(D-lactic acid), poly(D,L-lactic acid), poly(L-lactic acid), poly(D-lactic acid-co-glycolic acid), poly(D,L-lactic acid-co-glycolic acid), and poly(L-lactic acid-co-glycolic acid), respectively. Similarly, for other copolymers, the terms D-lactide, D,L-lactide, and L-lactide are used interchangeably with the terms D-lactic acid, D,L-lactic acid, and L-lactic acid, respectively.

As used herein, caprolactone includes, but is not limited to, ε-caprolactone.

In any embodiments of the present invention described herein, a disclosure of a polymer including lactide encompasses embodiments where the lactide may be L-lactide, D-lactide, D,L-lactide, meso-lactide, or a combination thereof.

Polymers, oligomers, or materials that are biosoluble are preferred. Non-limiting examples of these polymers include polyethylene glycol, polyethylene oxide, polyvinylpyrrolidone (PVP), polyacrylic acid, poly(methacrylic acid), polyvinyl alcohol (PVA), poly[N-(2-hydroxypropyl)methacrylamide] (poly(HPMA)), silk-elastin, elastin mimetic peptides, alginic acid, alginate, chondroitin sulfate, chitosan, chitosan sulfate, collagen, fibrin, fibrinogen, cellulose, cellulose sulfate, carboxymethylcellulose, hydroxyl cellulose, hydroxypropyl cellulose (HPC, HPC-SL, and HPC-L), hydroxypropyl methylcellulose (HPMC), carboxymethylcellulose sodium, hydroxy-ethylcellulose, gelatin, sugars, starch, starches (such as hydroxyethyl starch and 2-O-acetyl starches), polysaccharides, dextran sulfate, dextran, dextrin, xanthan, hyaluronic acid, fragments of hyaluronic acid, polysaccharides, and phosphoryl choline containing polymers.

Some examples of sugars and sugar derivatives that may be used in the embodiments of the present invention include, without limitation, sucrose, dextrose, lactose, maltodextrins, sorbitol, xylitol, maltose, glucose, sucrose, mannose, trehalose, corn syrup, and molasses.

Other preferred polymers and oligomers include, without limitation, block copolymers in which polyethylene glycol (PEG) forms one of the blocks. Many of these polymers are biosoluble. Preferred block copolymers in which polyethylene glycol (PEG) forms one of the blocks are those in which the polyethylene glycol (PEG) block(s) are at least 25 weight % (wt %), preferably at least 30 wt %, and in some embodiments, at least 40 wt %, and not more than 95 wt % of the block copolymer. Examples of these polymers include, without limitation, polyethylene glycol-poly(lactide-co-glycolide-co-caprolactone)-di- and tri-block copolymers, polyethylene glycol-poly(trimethylene carbonate-co-glycolide)-di- and tri-block copolymers, polyethylene glycol-poly(caprolactone)-di- and tri-block copolymers (PEG-PCL), polyethylene glycol-polylactide di- and tri-block copolymers (PEG-PLA), and polyethylene glycol-poly(lactide-glycolide) di- and tri-block copolymers (PEG-PLGA), where the lactide may be L-lactide, D-lactide, D,L-lactide, meso-lactide, or a combination thereof.

Other polymers include block copolymers of polyethylene oxide and polypropylene oxide, most of which are surfactants. The term "poloxamer" (CAS no. 9003-11-6) refers to tri-block copolymers with a central block of poly (propylene oxide) (PPO) and with a block of poly(ethylene oxide) (PEO) on each side where the PEO blocks are usually of the same length in terms of number of constitutional units. These polymers have the formula: $HO(C_2H_4O)_a(C_3H_6O)_b(C_2H_4O)_aH$ where "a" and "b" denote the number of polyethylene oxide and polypropylene oxide units, respectively. Poloxamers of types 124, 188, 237, 338, and 407 are specified by a monograph in the National Formulary. Other poloxamers that may be used, include, without limitation, types 108, 217, 238, and 288. Some PLURONIC® polymers sold by BASF also meet one of the NF specifications for a type of poloxamer.

Other polymers include block copolymers with polyethylene oxide block(s) and polypropylene oxide block(s) arranged as a di-block or a tri-block which is further covalently attached to one or more blocks of one or more monomers, the constituent monomers being selected from the group consisting of L-lactide, D-lactide, D,L-lactide, meso-lactide, glycolide, trimethylene carbonate, caprolactone, and combinations thereof.

In some embodiments, the PEG, polyethylene oxide/polypropylene oxide block, or both, are replaced by poly (vinyl pyrrolidone), poly(vinyl alcohol), a combination thereof, or either one or both covalently combined with PEG or polyethylene oxide/polypropylene oxide.

Preferred weight-average molecular weights for polymers used as coatings on the devices of this invention are from 25,000 to 750,000 grams/mole.

Therapeutic Agents

Therapeutic agents that may be suitable for use in the embodiments of the present invention, either individually or in combination, depending, of course, on the specific disease being treated, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective therapeutic agents.

The term "anti-proliferative" as used herein, refers to a therapeutic agent that works to block the proliferative phase of acute cellular rejection. The anti-proliferative therapeutic agent can be a natural proteineous substance such as a cytotoxin or a synthetic molecule. Other therapeutic agents include, without limitation, anti-proliferative substances such as actinomycin D, or derivatives thereof (manufactured by Sigma-Aldrich 1001 West Saint Paul Avenue, Milwaukee, Wis. 53233; or COSMEGEN™ available from Merck) (synonyms of actinomycin D include dactinomycin, actinomycin IV, actinomycin actinomycin $X_1$, and actinomycin $C_1$) all taxoids such as taxols, docetaxel, and paclitaxel, paclitaxel derivatives, FKBP-12 mediated mTOR inhibitors, and pirfenidone. Other anti-proliferative therapeutic agents include, without limitation, rapamycin (sirolimus), everolimus, zotarolimus (ABT-578), biolimus A9, ridaforolimus (formerly deforolimus, and also known as AP23573), tacrolimus, temsirolimus, pimecrolimus, novolimus, myolimus, umirolimus, merilimus, 40-O-(3-hydroxypropyl)rapamycin, 40-O-[2-(2-hydroxy)-ethoxy]ethyl-rapamycin, 40-O-tetrazolylrapamycin, and 40-epi-(N1-tetrazolyl)-rapamycin. Other compounds that may be used as therapeutic agents are those compounds having the structure of rapamycin but with a substituent at the carbon corresponding to the 42 or 40 carbon (see structure below).

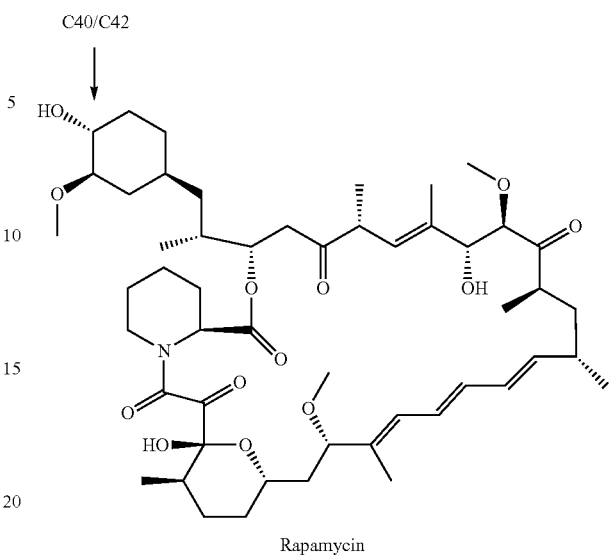

Rapamycin

Additional examples of cytostatic or antiproliferative therapeutic agents include, without limitation, angiopeptin, and fibroblast growth factor (FGF) antagonists.

Examples of anti-inflammatory therapeutic agents include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexamethasone phosphate, mometasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Alternatively, the anti-inflammatory therapeutic agent can be a biological inhibitor of pro-inflammatory signaling molecules. Anti-inflammatory therapeutic agents may be bioactive substances including antibodies to such biological inflammatory signaling molecules.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin therapeutic agents include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide, nitric oxide donors, super oxide dismutases, super oxide dismutase mimetic and 4-amino-2,2,6,6-tetramethylpiperidine-1-oxyl (4-amino-TEMPO).

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other therapeutic agents that may be used, include, without limitation, estradiol, 17-beta-estradiol, γ-hiridun, imatinib mesylate, midostaurin, feno fibrate, and feno fibric acid.

Other therapeutic agents that have not been specifically listed may also be used. Some therapeutic agents may fall into more than one of the above mentioned categories. Prodrugs thereof, co-drugs thereof, and combinations thereof of the above listed drugs are also encompassed in the various embodiments of the present invention.

Method of Treating or Preventing Disorders

Embodiments of the present invention encompass methods of treating a patient (an animal, expressly including a human) with a coated medical device wherein the coating may be any one of the embodiments, or any combination of embodiments of the present invention, or formed by any embodiment or combination of embodiments of the present invention. In particular, an implantable device with a coating as described herein may be used to treat, prevent, mitigate, reduce, diagnose, or any combination thereof various conditions or disorders, or to provide a pro-healing effect. Non-limiting examples of such conditions or disorders include: coronary artery disease, carotid artery disease, peripheral arterial disease, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction, benign pancreatic disease, and tumor obstruction tumors (in, for example, the esophagus, the trachea/bronchi, etc.).

EXAMPLES

The examples presented in this section are provided by way of illustration of the current invention only and are not intended nor are they to be construed as limiting the scope of this invention in any manner whatsoever.

Example 1

SUPERA™ VERITAS™ peripheral stent system, a stent formed of woven nitinol wires, was used as the coating substrate. The full length segmented stent is 150 mm, but in these examples, one segment of 38 mm was used as the substrate. All stents were cleaned prior to coating. The spraying operation was carried out with a custom made spray coater equipped with a spray nozzle, a drying nozzle, and a means to rotate and translate the stent under the nozzles. A stent holding fixture held the stent under the spray and drying nozzles.

Example 1A

Stents were coated with a primer layer of poly(vinylidene fluoride-co-hexafluoro-propylene) (PVDF-HFP) applied by spraying a coating solution of 1 to 2 wt % of PVDF-HFP in a solvent formed by blending acetone and cyclohexane in a 70:30 weight:weight mixture. The drug reservoir layer was formed by spraying a solution of everolimus (supplied by Novartis) and PVDF-HFP from a solution of a solvent formed by blending acetone and cyclohexane in a 70:30 weight:weight mixture, with 2 wt % polymer, and a drug to polymer weight ratio of 1:4.9. Multiple passes of the spray nozzle and drying nozzle were required to reach the target weight for both the primer and the drug reservoir layer.

Example 1B

Stents were coated with a primer layer of poly(D, L-lactic acid) (PDLLA), provided by Boehringer Ingelheim, which was applied by spraying a coating solution of 2 wt % of PDLLA in acetone. The drug reservoir layer was formed by spraying a solution of everolimus (supplied by Novartis) and PDLLA from a solution of acetone with 2 wt % polymer, and a drug to polymer weight ratio of 1:1. Multiple passes of the spray nozzle and drying nozzle were required to reach the target weight for both the primer and the drug reservoir layer.

Particulate Testing

For particulate testing, four (4) coated stents from Example 1B were "deployed" in a 6 mm inner diameter (ID) silicone tube and the deployed stents were subjected to a flow of phosphate buffered saline (pH of 7.4±0.2) (PBS) to simulate in-vivo conditions. The PBS was collected, and the number of particles in the fluid was determined. The number of particles in the solution was determined using a HIAC ROYCO™ particle counter which provides the number of particles in various size ranges. For the 4 stents tested, the number of particles having a diameter (hydrodynamic diameter) of greater than 10 μm was 202.5, and the number of particles having a diameter of greater than 25 μm was 33.8.

Particles "shed" from an implant in the blood vessel are a concern as larger, non-bioabsorbable particles may present an embolism risk.

Scanning Electron Microscopy

Coated stents from Examples 1A were crimped in the same manner as the stents would be crimped onto a balloon of a balloon catheter for delivery, and "deployed" to simulate in-vivo delivery and deployment. Subsequently photographs of the coating were taken with the coated stent under scanning electron microscope (SEM). The SEM images showed some coating abrasion at the junctions, but no tears or coating losses.

Axial Fatigue Testing

Coated stents from Examples 1B were crimped in the same manner as the stents would be crimped onto a balloon of a balloon catheter for delivery, expanded ("deployed"), and then subjected to axial fatigue testing. Axial fatigue testing is accomplished by repeatedly compressing (shortening the length, not crimping) the stent axially and then lengthening the stent with a concomitant decrease in the diameter to simulate in-vivo use. A large number of repetitions were performed. Subsequently photographs of the coating were taken with the coated stent under scanning electron microscope (SEM). The SEM images showed some coating defects, and shedding. Most of the shedding occurred on the luminal side of the sent.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation, and in which it is obvious to those skilled in the art that inclusion of that aspect is not illogical. In like manner, a recitation of an aspect as composing part of an embodiment is a tacit recognition that a supplementary embodiment exists in that specifically excludes that aspect.

What is claimed is:

1. A method comprising:
preparing a coating composition comprising one or more solvents, one or more polymers, and optionally one or more therapeutic agents;
subsequent to the preparation, applying the coating composition onto a medical device from an applicator to form a coating layer upon substantial removal of the solvent(s), the application comprising two or more passes;
wherein the medical device is generally tubular in shape;
wherein during each pass
with respect to the applicator, the medical device axially translates;
with respect to the applicator, the medical device rotates;
or a combination thereof;
and
wherein the medical device is twisted, and
with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 5%.

2. The method of claim 1, wherein the diameter of the medical device varies during the application process, such that the largest diameter during any pass differs from the smallest diameter in any pass by at least 5%.

3. The method of claim 2, wherein the variation of the diameter is continuous.

4. The method of claim 2, wherein the diameter of the medical device varies during the application process, the variation ranging such that the largest diameter during any pass differs from the smallest diameter in any pass by at least 20%.

5. The method of claim 2, wherein the diameter of the medical device varies during the application process, the variation ranging such that the largest diameter during any pass differs from the smallest diameter in any pass by at least 40%.

6. The method of claim 2, wherein the medical device is held at a first diameter for at least one pass; and then, the medical device is held at a second diameter for at least one pass.

7. The method of claim 2, wherein the medical device is a braided stent; and wherein the variation in the stent diameter results from stretching the stent, compressing the stent, or a combination of stretching and compressing the stent in the axial direction.

8. The method of claim 1, wherein the twisting is continuous.

9. The method of claim 1, wherein with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 15%.

10. The method of claim 1, wherein with respect to one end of the medical device, the degree of twist of the other end varies during the application process, such that the difference between the largest degree of twist in one direction in any pass and the largest degree of twist in the opposite direction in any pass, or if no twist in the opposite direction, the smallest degree of twist in the same direction in any pass, is at least 30%.

11. The method of claim 1, wherein the medical device is twisted either counterclockwise or clockwise to an angular position and held for at least one pass, and the medical device twisted back to the original conformation of no twist, twisted back to a different angular position, or twisted back to the original conformation and subsequently twisted in the opposite direction, and held for at least one pass.

12. The method of claim 1, wherein the tubularly shaped medical device is a stent.

13. The method of claim 12, wherein the stent is a braided stent.

14. The method of claim 1, wherein at least one polymer is selected from the group consisting of poly(ethylene glycol) (PEG), poly(ethylene-oxide), block copolymers of poly (ethylene-oxide) and poly(propylene oxide), poly(lactide-co-glycolide-co-caprolactone)-block-PEG-poly(lactide-coglycolide-co-caprolactone) polymers, poly(trimethylene carbonate-co-glycolide)-block-PEG-block-poly(trimethylene carbonate-co-glycolide) polymers, polylactide-block-PEG-polylactide polymers, poly(trimethylene carbonate-co-glycolide)-block-PEG-poly(trimethylene carbonate-co-glycolide) polymers, and poly(lactide-co-glycolide)-block-PEG-blockpoly(lactide-co-glycolide) polymers.

15. The method of claim 1, wherein the coating composition comprises at least one therapeutic agent.

16. The method of claim 15, wherein the therapeutic agent is selected from the group consisting of dexamethasone, Biolimus A9, ridaforolimus, tacrolimus, temsirolimus, pimecrolimus, novolimus, myolimus, zotarolimus everolimus, 40-O-(3-hydroxypropyl)rapamycin, 40-O-[2(2-hydroxy) ethoxy]ethyl-rapamycin, 40-O-tetrazolylrapamycin, 40-epi-(N1-tetrazolyl)-rapamycin, and combinations thereof.

17. A method comprising:
applying one or more first solvents onto a medical device surface;
wherein the combination of the one or more first solvents has a viscosity of about equal to or greater than 45 cP, a surface tension of about equal to or greater than 45 mN/m, or both; and
wherein the one or more first solvents are substantially free of other materials;
preparing a coating composition comprising one or more second solvents, one or more polymers, and optionally one or more therapeutic agents;
wherein each of the one or more second solvents may be the same as any one of the one or more first solvents, or may be different from each of the one or more first solvents;
subsequent to the preparation and the application of the one or more first solvents, disposing the coating composition over the medical device surface to form a coating layer upon substantial removal of the solvent(s).

* * * * *